United States Patent
Larsen (10) Patent No.: US 10,556,066 B2
(45) Date of Patent: Feb. 11, 2020

(54) POWER EFFICIENT ELECTRONIC DEVICE

(71) Applicant: Novo Nordisk A/S, Bagsvaerd (DK)

(72) Inventor: Andre Larsen, Dragoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 218 days.

(21) Appl. No.: 15/575,864

(22) PCT Filed: May 26, 2016

(86) PCT No.: PCT/EP2016/061930
§ 371 (c)(1),
(2) Date: Nov. 21, 2017

(87) PCT Pub. No.: WO2016/193122
PCT Pub. Date: Dec. 8, 2016

(65) Prior Publication Data
US 2018/0117259 A1    May 3, 2018

(30) Foreign Application Priority Data

May 29, 2015  (EP) .................. 15169922

(51) Int. Cl.
*A61M 5/315* (2006.01)
*H01M 12/06* (2006.01)
(Continued)

(52) U.S. Cl.
CPC ...... *A61M 5/31568* (2013.01); *A61M 5/2046* (2013.01); *A61M 5/3155* (2013.01); *H01M 6/36* (2013.01); *H01M 12/06* (2013.01); *A61M 5/3146* (2013.01); *A61M 5/3202* (2013.01); *A61M 2205/50* (2013.01); *A61M 2205/52* (2013.01); *A61M 2205/8206* (2013.01); *H01M 2220/30* (2013.01)

(58) Field of Classification Search
CPC ........ A61M 5/142; A61M 2005/14208; A61M 2205/8206
See application file for complete search history.

(56) References Cited

U.S. PATENT DOCUMENTS 4,902,278 A   2/1990  Maget et al.
5,788,682 A * 8/1998  Maget .............. A61F 13/00063
                                                        604/290
(Continued)

FOREIGN PATENT DOCUMENTS

WO   2004/030727 A2   4/2004
WO   2007107564 A1    9/2007
(Continued)

*Primary Examiner* — Laura A Bouchelle
(74) *Attorney, Agent, or Firm* — Wesley Nicolas (57) ABSTRACT

An assembly comprises an electric consumer, an electric voltage source adapted to power the electric consumer, and user operated actuation means. The electric voltage source is operable between a first state in which a first voltage is generated and a second state in which a second higher voltage is generated. The user operated actuation means is operable from a first to a second state and adapted to thereby operate the electric voltage source from the first to the second state, and operable from the second state to the first state and adapted to thereby operate the electric voltage source from the second to the first state.

13 Claims, 4 Drawing Sheets

(51) Int. Cl.
*H01M 6/36* (2006.01)
*A61M 5/20* (2006.01)
A61M 5/31 (2006.01)
A61M 5/32 (2006.01)

(56) References Cited

U.S. PATENT DOCUMENTS

| | | | |
|---|---|---|---|
| 6,010,317 A | 1/2000 | Maget et al. | |
| 7,794,426 B2 * | 9/2010 | Briones | A61M 5/1413 604/131 |
| 8,287,514 B2 | 10/2012 | Miller et al. | |
| 8,728,024 B2 * | 5/2014 | Kamen | A61M 39/14 604/65 |
| 2007/0073235 A1 | 3/2007 | Estes et al. | |
| 2009/0318865 A1 | 12/2009 | Moller et al. | |

FOREIGN PATENT DOCUMENTS

| | | |
|---|---|---|
| WO | 2010037828 A1 | 4/2010 |
| WO | 2010052275 A2 | 5/2010 |
| WO | 2015/071354 A1 | 5/2015 |

* cited by examiner

POWER EFFICIENT ELECTRONIC DEVICE

CROSS-REFERENCE TO RELATED APPLICATIONS

This application is a 35 U.S.C. § 371 National Stage application of International Application PCT/EP2016/061930 (published as WO 2016/193122), filed May 26, 2016, which claims priority to European Patent Application 15169922.0, filed May 29, 2015; the contents of which are incorporated herein by reference.

The present invention generally relates to portable electronic devices provided with a power source. In specific embodiments the power source may be non-rechargeable and non-replaceable.

BACKGROUND OF THE INVENTION

In the disclosure of the present invention reference is mostly made to drug delivery devices used e.g. in the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from which the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems based on the assumption that ejected doses corresponds to injected doses.

Addressing this need injection devices integrating a monitoring/acquisition mechanism into the device itself have been proposed, e.g. as disclosed in US 2009/0318865 and WO 2010/052275. Alternatively, the desired functionality may be provided by an electronic "add-on" module adapted to be attached to and measure signals generated by a standard mechanical pen device, e.g. as disclosed in WO 2007/107564 and EP2014/074475.

To keep costs down and to make such devices simple to use it may be desirable to provide devices which do not need to be recharged. Correspondingly, such devices are normally equipped with either a replaceable battery or a power source with a capacity to last the expected lifetime of the device.

Some devices may however have a significant storage time from production to first use and furthermore a very limited time of actual use compared to in-between use time. Therefore such devices often have their power source disconnected from the electronics while stored and go into sleep-mode between uses. Since all power sources to some extend discharge over time and needs to power at least part of the electronics between uses in order to be able to "wake-up" from sleep-mode, it is often necessary to equip a device with a power source of more than ten times the actual required capacity, because more than 90% of the power is used during storage and in between uses.

Having regard to the above, it is an object of the present invention to provide an assembly with a power source which for a given size/capacity of the power source has improved storage time as well as improved use time. The assembly may be in the form of a portable electronic device. The device should be user-friendly and adapted for cost-effective manufacturing.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention an assembly is provided, comprising an electric consumer, an electric voltage source adapted to power the electric consumer, and operatable between a first state in which a first voltage is generated and a second state in which a second higher voltage is generated, as well as user operated actuation means. The user operated actuation means is operatable from a first to a second state and adapted to thereby operate the electric voltage source from the first to the second state, and is operatable from the second state to the first state and adapted to thereby operate the electric voltage source from the second to the first state.

By this arrangement an assembly is provided which for a given size/capacity of the power source has improved storage time as well as improved use time. In an exemplary embodiment the first voltage is at least 5 times lower than the second voltage. In a specific embodiment the first voltage is zero.

It should be emphasized that the invention provides a regulated voltage source and not merely a regulated voltage supply with e.g. a transformer as known from e.g. WO 2004/030727.

The electric voltage source may be in the form of a chemical electric cell in which the chemical process utilizes a component for generating the voltage, and the electric voltage source is operated between the first and the second state by controlling the supply of the component.

The controlled component may be a gas and the actuation means may be adapted to in the first state to allow a first flow rate of gas to the electric voltage source, and in the second state to allow a second higher flow rate of gas to the electric voltage source.

The first flow rate may be at least 5 times lower than the second flow rate. In a specific embodiment the first flow rate may for all practical purposes be zero.

The assembly may comprise a gas conduit for supplying the component gas to the electric voltage source, the conduit being flushed with the component gas when the actuation means is operated from the first to the second state.

In an exemplary embodiment the assembly is in the form of a drug delivery device comprising a main portion provided with a drug reservoir or means for receiving a drug reservoir, the reservoir comprising an outlet portion, dose setting means, expelling means for expelling a set dose of drug from the reservoir, the electric voltage source, and the electric consumer in the form of electronic circuitry. The device further comprises a cap adapted to be mounted on the main portion to thereby cover the reservoir outlet portion.

In a specific embodiment the electronic circuitry comprises sensor means adapted to capture a property value related to a dose amount of drug expelled from a reservoir by the expelling means during an expelling event, processor means adapted to determine dose amounts based on captured property values, storage means adapted to store at least one dose amount, as well as display means adapted to display a determined dose amount and/or a time value.

The actuation means for the above-described devices may be in the form of the cap, the electric voltage source being operated from the first to the second state and from the second to the first state when the cap is removed from the main portion respectively mounted on the main portion.

In a further aspect of the invention a method of operating an assembly is provided, comprising the steps of (i) providing an assembly comprising an electric consumer, an electric voltage source adapted to power the electric consumer, and being operatable between a first state in which a first voltage is generated and a second state in which a second higher voltage is generated, and user operated actuation means, (ii) operate the actuation means from a first to a second state to thereby operate the electric voltage source from the first to the second state, and (iii) operate the actuation means from the second state to the first state to thereby operate the electric voltage source from the second to the first state.

The electric voltage source may be a chemical electric cell utilizing a gas for generating the voltage, and the electric voltage source may be operated between the first and the second state by controlling the supply of the gas.

The actuation means in the first state may allow a first flow rate of gas to the electric voltage source, and the actuation means in the second state may allow a second higher flow rate of gas to the electric voltage source.

The assembly may further comprise a gas conduit for supplying the component gas to the electric voltage source, and the step of operating the actuation means from the first to the second state may include flushing the conduit with the component gas.

In the context of the present application and as used in the specification and the claims, the term processor means covers any combination of electronic circuitry suitable for providing the specified functionality, e.g. processing and storing data as well as controlling all connected input and output devices. A processor will typically comprise one or more CPUs or microprocessors which may be supplemented by additional devices for support, storage or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or OLED.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following exemplary embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to aspects of the invention per se an electric voltage source (or power source) suitable for forming part of the present invention will be described. The electric voltage source is adapted to power an electric consumer, and is operatable between a first state in which a first voltage is generated and a second state in which a second higher voltage is generated. Although the described power source is in the form of a single-cell voltage generating unit also the term "battery" will be used.

Such a power source is provided by a chemical battery in which one of the necessary components of the battery is not introduced until power is needed, e.g. until first use of a given device. This will eliminate the self-discharge during storage and distribution between production and first use. If the amount of the necessary component introduced to make the battery work is furthermore limited to provide only enough power for one actual use, the battery can "wear out" soon after actual use and become inactive until next introduction of necessary component and subsequent use.

Figure 1:
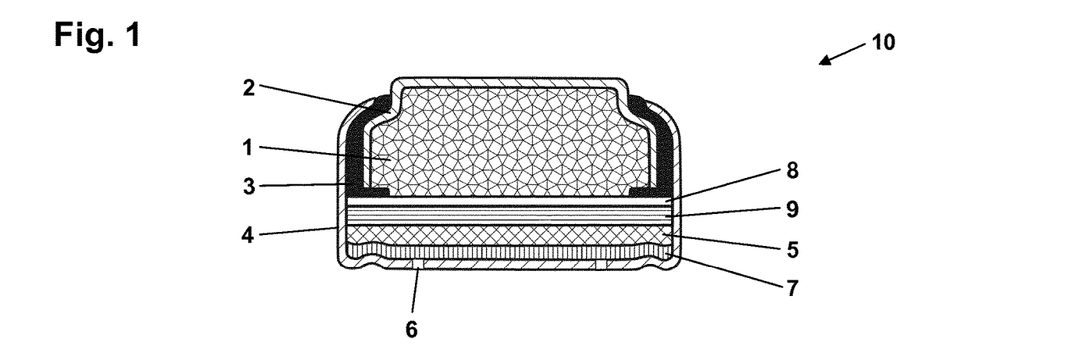
FIG. 1 shows in a cross-sectional view a schematic representation of a zinc-air battery.

An example of such a source is zinc-air batteries which can be deprived of air and thus be inactive until first use. FIG. 1 shows in cross-section a schematic representation of a zinc-air battery in which zinc powder 1 mixed with an electrolyte is partly contained in an anode can 2 and is electrically separated from an outer cathode can 4 by an insulator 3. The outer can is provided with a number of air holes 6 which prior to use are sealed, e.g. by a peelable seal (not shown) which can be removed when taken into first use. Air will then be able to enter through the air holes 6, through a semi permeable membrane 7 and into an air distribution layer 5. The purpose of the semi permeable membrane is to allow moist air to enter, but prevent the escape of moisture/water from the electrolyte. A separator 8 prevents short circuiting the zinc powder anode 1 and a cathode catalyst 9 that also acts as a current collector. When oxygen from the air reacts at the cathode 9 hydroxyl is formed and ions migrate into the zinc anode 1 and form zincate (Zn(OH)2-4) releasing electrons that travel to the cathode 9. The zincate decays into zinc oxide and water returns to the electrolyte. The water and hydroxyl from the anode are recycled at the cathode, so the water is not consumed.

Figure 2A:
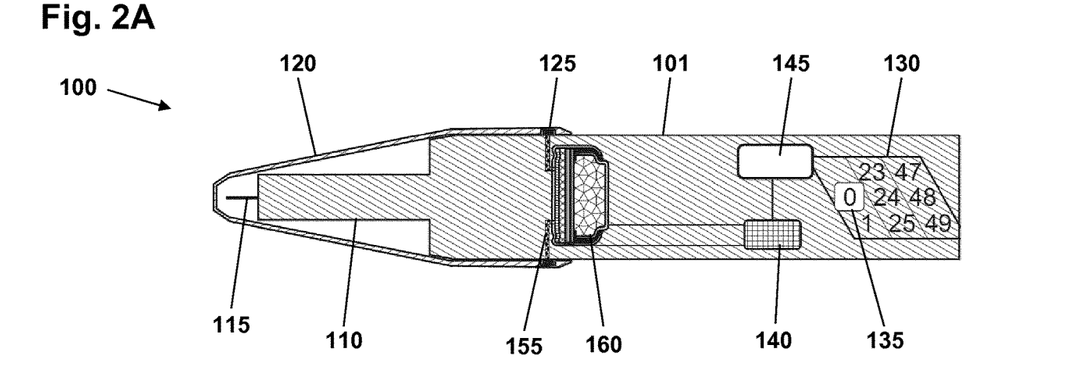
FIGS. 2A and 2B show in cross-sectional views a schematic representation of a first embodiment of a drug delivery device in different operational states.

FIG. 2A shows in schematic form a pen-formed drug delivery device 100 comprising a drug reservoir 110 with an outlet 115, a detachable cap 120 adapted to cover the drug reservoir outlet portion in a mounted position on the device body portion 101, and drug expelling means comprising dose setting means allowing a user to set a dose amount of drug to be expelled, the set dose printed on a rotatable scale drum 130 being shown in a window 135. The device is provided with electronic circuitry 140 comprising sensor means adapted to capture a property value related to the dose amount of drug expelled from the reservoir by the expelling means during an expelling event, processor means adapted to determine dose amounts based on captured property values, storage means adapted to store at least one dose amount, display means 145 adapted to display dose related information, e.g. a determined dose amount and a related time value, and a power source 160. As appears, the drug expelling means and the electronic circuitry are only shown schematically but could be of any suitable design, e.g. as described in WO 2014/128156.

Figure 2B:
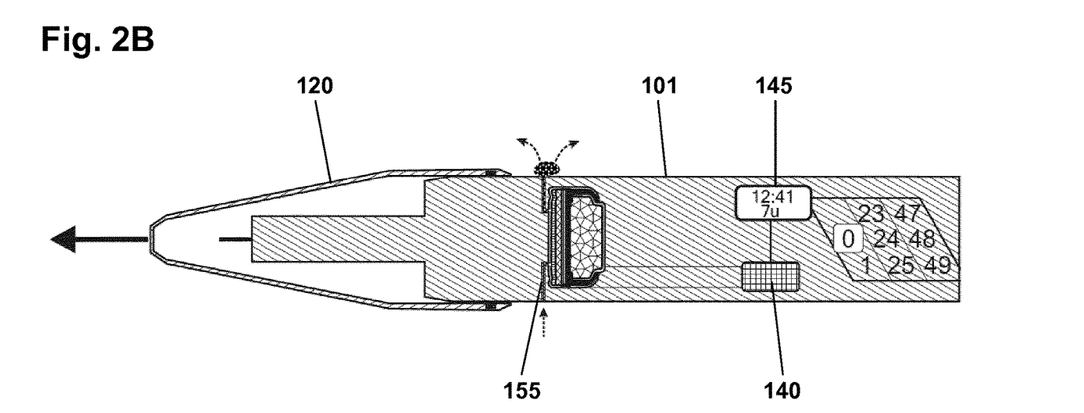

The power source is in the form of a zinc-air battery of the type described with reference to FIG. 1 and comprises a number of air holes in communication with the exterior through one or more channels 155 formed between the battery and openings formed in the pen body exterior surface. The pen cap is provided with sealing surface portions 125 adapted to seal the openings when the cap is in a fully mounted position as shown in FIG. 2A. When the cap 120 is removed fully or partly from the device body portion 101 as shown in FIG. 2B the channel openings are exposed and communication is established between the battery air holes and the exterior, this allowing oxygen-rich air to enter the battery whereby the above-described chemical process starts and a voltage is generated, this allowing the electronic circuitry 140 to power up and to register an expelled dose which then may be displayed in the display means 145. If no dose is expelled the display may show the last expelled dose and the time since then, this being a normal use scenario when the user just wants to check when the last dose was expelled.

As appears from the above, it is necessary that the system powers up before a given dose is set and expelled. Correspondingly, the specific design and dimensions of the air channels should be optimized for a swift supply of fresh air. The shown channels as well as the shown arrangement with an inlet and an outlet are for illustrative purposes only. The electronics may be set up to turn on an indicator in the display when the system has powered up, this informing the user that the system is ready to register a dose to be expelled.

If only a limited amount of air is let into the battery, the oxygen will be used up after a given time after the cap has been fully mounted again thereby sealing the channel openings. As the voltage drops the electronic circuitry will power off automatically and no sleep current or self-discharge of the battery occur during in-between use time. When the cap is removed from the injection device to perform the next injection or to check the display, the battery is supplied with a small amount of air/oxygen sufficient to power the next injection logging and power of again when the limited amount of oxygen in the battery is used.

Addressing the issue of power-up time, a further embodiment of a drug delivery device of the type described with reference to FIG. 2A will be described with reference to FIG. 3, the two embodiments having the same type of dose setting and expelling means as well as the electronics.

Figure 3:
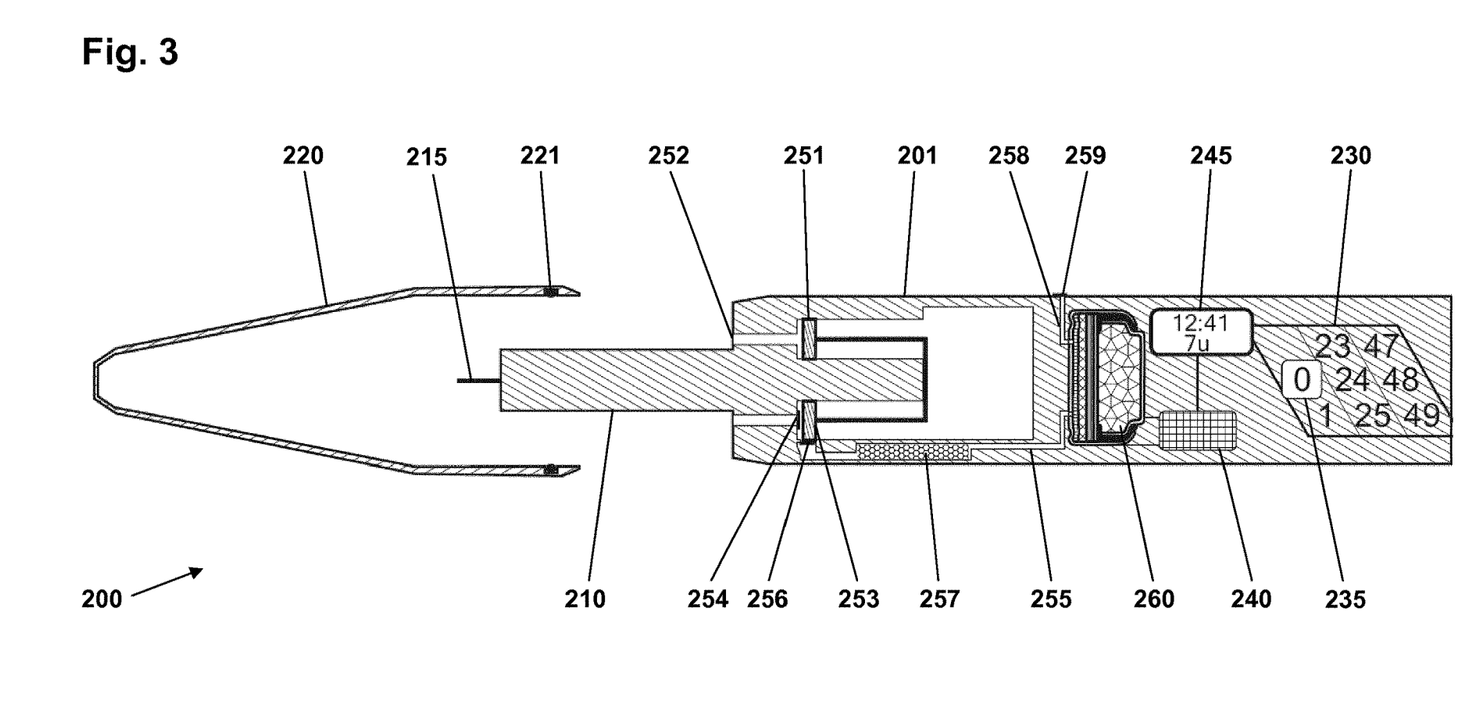
FIG. 3 shows in a cross-sectional view a schematic representation of a second embodiment of a drug delivery device.

Correspondingly, FIG. 3 shows in schematic form a pen-formed drug delivery device 200 comprising body portion 201, a drug reservoir 210 with an outlet 215, a detachable cap 220 adapted to be mounted on the body portion to cover the drug reservoir outlet portion in a mounted position, and drug expelling means comprising dose setting means allowing a user to set a dose amount of drug to be expelled, the set dose printed on a rotatable scale drum 230 being shown in a window 235. The cap comprises a circumferential seal 221 adapted to slidingly engage the outer body surface, a sealed space thereby being created inside cap. The device is provided with electronic circuitry 240 comprising sensor means adapted to capture a property value related to the dose amount of drug expelled from the reservoir by the expelling means during an expelling event, processor means adapted to determine dose amounts based on captured property values, storage means adapted to store at least one dose amount, a display 245 adapted to display dose related information, e.g. a determined dose amount and a related time value, and a power source in the form of a zinc-air battery 260.

However, in contrast to the relatively simple air channel arrangement of the first embodiment, the second embodiment is provided with a forced air purging system operated by the cap. More specifically, the purging system comprises an actuator piston 251 arranged in an actuator cylinder with an air flow opening 252, and a working piston 253 arranged in a working cylinder with an air inlet provided with an inlet valve 254, an air chamber 250 being formed between the working piston and the inlet valve (see FIG. 4A). The two pistons are interconnected and thus moving in tandem. The working cylinder is connected to the power source via an air inlet channel 255 provided with an actuation inlet valve 256, an air moisturizer 257 being arranged in the air inlet channel. An air exhaust channel 258 with an air outlet valve 259 connects the power source with the exterior. With reference to FIGS. 4A-4D the working principle of the second embodiment will be described.

Figure 4A:
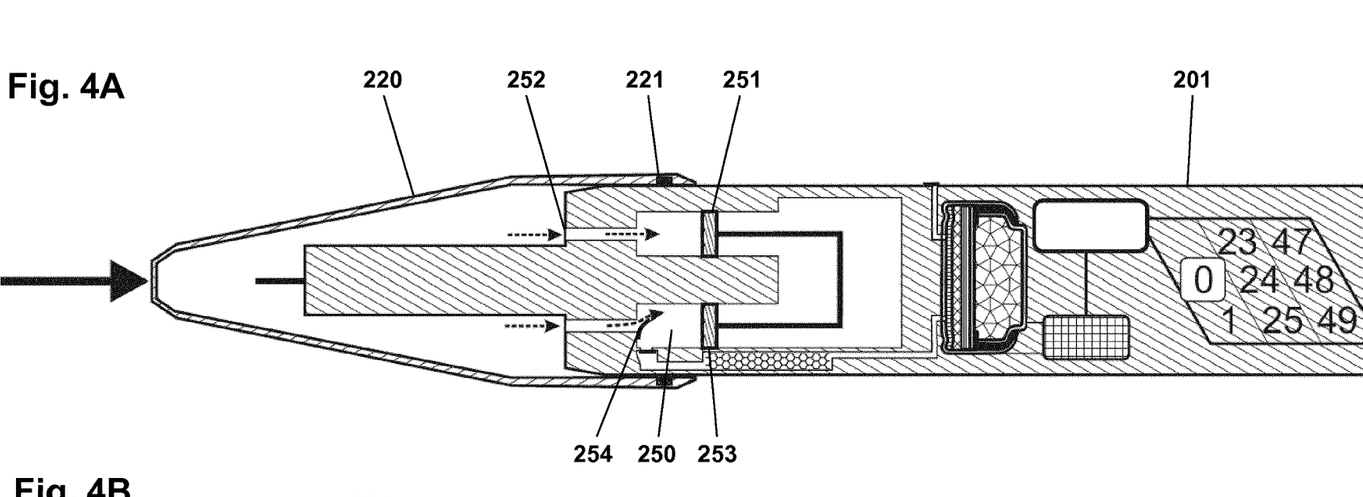
FIGS. 4A-4D show in cross-sectional views a schematic representation of the second embodiment of a drug delivery device in different operational states.
Figure 4B:
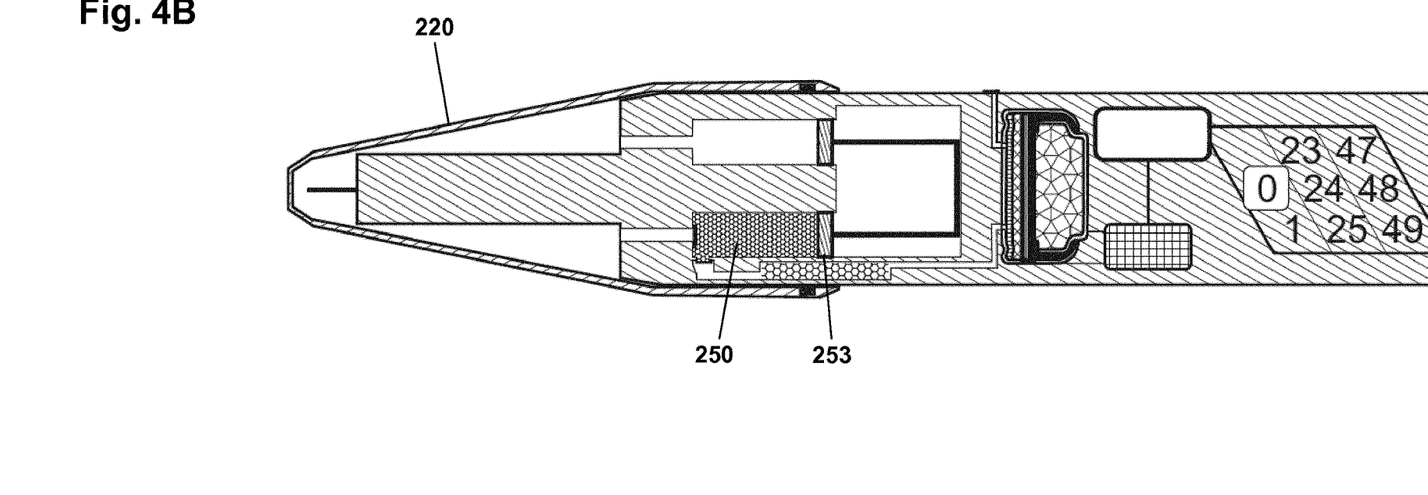

When the cap is mounted on the pen body as shown in FIG. 4A, the cap seal 221 ensures that air inside the cap is trapped and when the cap subsequently slides onto the device body portion 201 the air pressure inside the cap increases. The increased air pressure inside the cap forces air through the actuator cylinder air flow opening 252, this causing the actuator piston 251 to move proximally. As the two pistons are connected also the working piston 253 is moved proximally whereby the inlet valve 254 opens and fresh air flows into the working cylinder. Indeed, also the pressure inside the cap acts on the inlet valve and thus the working piston. When the working piston 253 is fully retracted as shown in FIG. 4B, a limited amount of fresh air is contained in the air chamber 250. The size of the air chamber is designed to contain only enough air to flush the zinc-air battery and provide oxygen for the expected time of use of a single use of the device (see below).

Figure 4C:
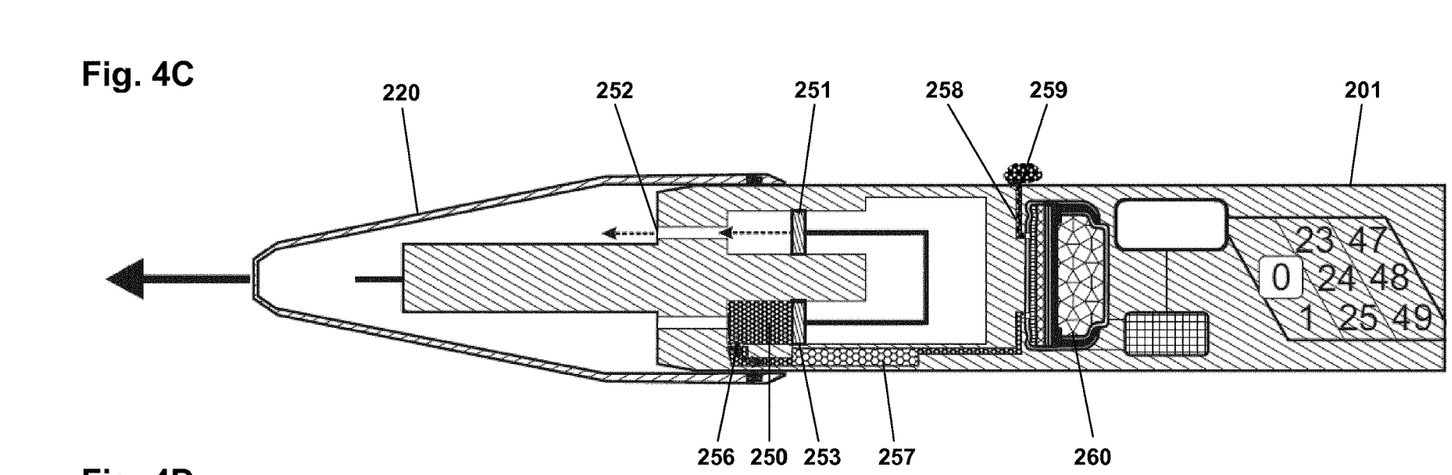
Figure 4D:
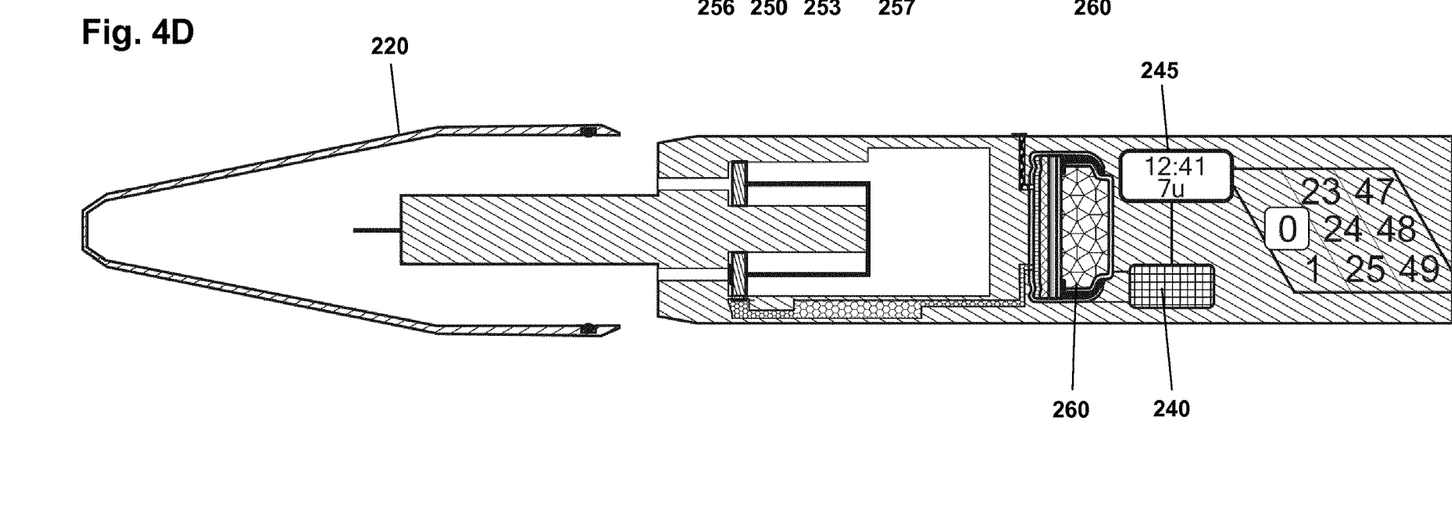

When the user starts removing the cap 220 as shown in FIG. 4C in order to use the device, pressure inside the cap is reduced. The resulting suction through the air flow opening 252 moves the actuator piston 251 as well as the thereto coupled working piston 253 distally, this resulting in air from the air chamber 250 being forced through the actuation inlet valve 256. The air then flows through the moisturizer 257 and the moist air proceeds via the inlet channel into the zinc-air battery 260 and flush out the oxygen deprived and carbon oxide contaminated air out through the exhaust channel 258 to the air outlet valve 259. In FIG. 4D the cap 220 has been fully removed and the air chamber air has been fully flushed. The fresh air provided to the zinc-air battery 260 activates the battery and the electric circuitry 240 is powered, allowing the electronic display 245 to display the information needed and the electronics of the device to work.

After use the user applies the cap again, thereby refilling the air chamber again and preparing the system for next use and required power-up. A while after use, the oxygen in the cell and air system is consumed and the battery becomes inactive and the display and electronics turn off.

With reference to FIG. 3 a first arrangement for flushing the battery with ambient air is described, however, this is just an example of a system operated by the attachment and removal of the device cap. As a further example the flushing could be driven by user actuation during dose setting, e.g. the rotation of a dose setting member could drive a "pump" arrangement. To provide a sufficient flow of gas, the latter may require a given minimum dose to be set, e.g. 10 units of insulin, which then subsequently can be adjusted to a lower value. Alternatively, a "power on" indicator may form part of the display as mentioned above.

For the above-described embodiments of the invention it is intended that the seal between the cap 120, 220 and the body portion 101, 201 is absolute, however, as this may be difficult to ensure completely under and during all circumstances, a given embodiment may be provided with an additional storage seal. For example, a battery cell of the type shown in FIG. 1 may be provided with a conventional pull-off seal which is removed before initial use. Alternatively, the above-described embodiments of a drug delivery device may be provided with an additional peelable seal between the cap and body portion which then is removed before initial use. During subsequent operational use of the assembly or device a seal being less than absolute may be acceptable.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An assembly comprising:
an electric consumer,
an electric voltage source adapted to power the electric consumer, and being operatable between a first state in which a first voltage is generated and a second state in which a second higher voltage is generated,
a main portion comprising:
a drug reservoir or structure for receiving a drug reservoir, the reservoir comprising an outlet portion,
a dose setting structure,
an expelling structure for expelling a set dose of drug from the reservoir,
the electric voltage source, and
the electric consumer in the form of electronic circuitry,
a cap adapted to be mounted on the main portion to thereby cover the reservoir outlet portion, and
a user operated actuation structure being:
operatable from a first to a second state and adapted to thereby operate the electric voltage source from the first to the second state, and
operatable from the second state to the first state and adapted to the re by operate the electricvoltage source from the second to the first state, wherein the actuation structure is in the form of the cap, the electricvoltage source being operated from the first to the second state and from the second to the first state when the cap is removed from the main portion and mounted on the main portion, respectively.

2. An assembly as in claim 1, wherein the first voltage is at least 5 times lower than the second voltage.

3. An assembly as in claim 1, wherein:
the electric voltage source is a chemical electric cell, the chemical process utilizing a component for generating the voltage, and
the electric voltage source is operated between the first and the second state by controlling the supply of the component.

4. An assembly as in claim 3, wherein the component is a gas.

5. An assembly as in claim 4, wherein:
the actuation structure in the first state allows a first flow rate of gas to the electric voltage source, and
the actuation structure in the second state allows a second higher flow rate of gas to the electric voltage source.

6. An assembly as in claim 5, wherein the first flow rate is at least 5 times lower than the second flow rate.

7. An assembly as in claim 5, wherein the first flow rate is zero.

8. An assembly as in claim 1, further comprising a gas conduit for supplying the component gas to the electric voltage source, the conduit being flushed with the component gas when the actuation structure is operated from the first to the second state.

9. An assembly as in claim 1, wherein the electronic circuitry comprises:
a sensor structure adapted to capture a property value related to a dose amount of drug expelled from a reservoir by the expelling structure during an expelling event,
a processor structure adapted to determine dose amounts based on captured property values,
a storage structure adapted to store at least one dose amount, and
a display structure adapted to display a determined dose amount and/or a time value.

10. A method of operating an assembly, comprising the steps of: providing an assembly comprising:
an electric consumer, an electric voltage source adapted to power the electric consumer, and being operatable between a first state in which a first voltage is generated and a second state in which a second higher voltage is generated, and user operated actuation structure, a main portion comprising:
- a drug reservoir or structure for receiving a drug reservoir, the reservoir comprising an outlet portion,
- a dose setting structure,
- an expelling structure for expelling a set dose of drug from the reservoir,
- the electric voltage source, and
- the electric consumer in the form of electronic circuitry, a cap adapted to be mounted on the main portion to thereby cover the reservoir outlet portion, and operate the actuation structure from a first to a second state to thereby operate the electric voltage source from the first to the second state, and operate the actuation structure from the second state to the first state to thereby operate the electric voltage source from the second to the first state, wherein the actuation structure is in the form of the cap, the electricvoltage source being operated from the first to the second state and from the second to the first state when the cap is removed from the main portion and mounted on the main portion, respectively.

11. A method of operating an assembly as in claim 10, wherein:
- the electric voltage source is a chemical electric cell utilizing a gas for generating the voltage, and
- the electric voltage source is operated between the first and the second state by controlling the supply of the gas.

12. A method of operating an assembly as in claim 11, wherein:
- the actuation structure in the first state allows a first flow rate of gas to the electric voltage source, and
- the actuation structure in the second state allows a second higher flow rate of gas to the electric voltage source.

13. A method of operating an assembly as in claim 11, wherein:
- the assembly further comprises a gas conduit for supplying the component gas to the electric voltage source, and
- the step of operating the actuation structure from the first to the second state includes flushing the conduit with the component gas.

* * * * *

UNITED STATES PATENT AND TRADEMARK OFFICE
CERTIFICATE OF CORRECTION

PATENT NO. : 10,556,066 B2
APPLICATION NO. : 15/575864
DATED : February 11, 2020
INVENTOR(S) : Andre Larsen It is certified that error appears in the above-identified patent and that said Letters Patent is hereby corrected as shown below:

In the Claims

At Column 8, Claim number 1, Please replace Line number 21 with the following:
"adapted to thereby operate the electric voltage"

At Column 8, Claim number 1, Please replace Line number 24 with the following:
"electric voltage source being operated from the first"

At Column 9, Claim number 10, Please replace Line number 23 with the following:
"the electric voltage source being operated from the first"

Signed and Sealed this
Twenty-ninth Day of December, 2020

Andrei Iancu
*Director of the United States Patent and Trademark Office*